United States Patent [19]

Cregge

[11] Patent Number: 5,374,632
[45] Date of Patent: Dec. 20, 1994

[54] 2,3-DIHYDRO-1-(8-METHYL-1,2,4-TRIAZOLO[4,3-B]-PYRIDAZIN-6-YL)-4(1H)-PYRIDINONE

[75] Inventor: Robert J. Cregge, Zionsville, Ind.

[73] Assignee: Merrell Dow Pharmaceuticals Inc., Cincinnati, Ohio

[21] Appl. No.: 931,644

[22] Filed: Aug. 17, 1992

Related U.S. Application Data

[63] Continuation of Ser. No. 426,451, Oct. 18, 1989, abandoned, which is a continuation of Ser. No. 871,011, Jun. 5, 1986, abandoned.

[51] Int. Cl.$^5$ .................... A61K 31/50; C07D 487/04
[52] U.S. Cl. .................... 514/248; 544/225; 544/230; 544/236
[58] Field of Search .................... 544/236; 514/248

[56] References Cited

U.S. PATENT DOCUMENTS

| | | | |
|---|---|---|---|
| 3,915,968 | 10/1975 | Bellasio | 544/236 |
| 4,136,182 | 1/1979 | Lewis | 544/236 |
| 4,366,156 | 12/1982 | Temple, Jr. | 514/267 |
| 4,489,078 | 12/1984 | Temple, Jr. | 514/257 |
| 4,515,791 | 5/1985 | Allen, Jr. et al. | 544/236 |
| 4,578,464 | 3/1986 | Cregge et al. | 544/236 |

OTHER PUBLICATIONS

"Advanced Organic Chemistry Part B: Reactions and Synthesis" by Carey and Sundberg (2nd Ed.) pp. 162, 163 (1983).
Abdallah et al., *Drug Development Research*, 7, pp. 185–193 (1986).
Haider et al., *Helv. Chim. Acta* 58, p. 1287 (1975).
Schell et al., *Synthetic Communications*, 12, pp. 755–761 (1982).
Yamazaki et al., *Chemical Abstracts*, vol. 94, No. 174823 (1981).
Winterfelot, *Ber.* 97 p. 2463 (1964).
"Aldrich Catalog Handbook of Fine Chemicals" p. 1098 (1986).
"The Merck Manual of Diagnosis and Therapy" (15th. Ed.) pp. 623–635 (1987).
Abdallah et al., Chemical Abstracts, 104: 180000x (1986).
Pfeifer et al., *Pharmazie*, 45, 609–614 (1990). (Translation is being provided.).
*Chemical Abstracts* 99, 194119h (1983).
Bucknell Lecture series (Dec. 1, 1982).
Thirty-first Annual Conference on Mass Spectrometry and and Allied Topics (Boston, 1983).
Thirty-third Annual Conference on Mass Spectrometry and and Allied Topics (San Diego, 1985).
Finnigan MAT Seminar Series (Cincinnati, Oct. 4, 1985).
H. J. Reich, *J. Org. Chem.* 39, 428 (1974).
K. B. Sharpless et al., *J. Org. Chem.*, 39, 429 (1974).
D. L. J. Clive, *Tetrahedron*, 34, 1049–50 and 1087–1090 (1978).

*Primary Examiner*—Emily Bernhardt
*Attorney, Agent, or Firm*—John J. Kolano; William J. Stein; Edlyn S. Simmons

[57] ABSTRACT

2,3-Dihydro-1-(8-methyl-1,2,4-triazolo [4,3-b]pyridazin-6-yl)-4(1H)-pyridinone has been prepared in substantially pure form and has been found to be useful for alleviating bronchial spasms in mammals. Synthesis of this material through phenylselenyl intermediates is described.

7 Claims, No Drawings

2,3-DIHYDRO-1-(8-METHYL-1,2,4-TRIAZOLO[4,3-B]-PYRIDAZIN-6-YL)-4(1H)-PYRIDINONE

This is a continuation of application Ser. No. 07/426,451, filed Oct. 18, 1989, now abandoned which is a continuation of application Ser. No. 871,011 filed Jun. 5, 1986, now abandoned.

BACKGROUND OF THE INVENTION

8-Methyl-6-(1-piperidinyl)-1,2,4-triazolo[4,3-b]pyridazine and its use in alleviating bronchial spasms have been described in U.S. Pat. Nos. 3,915,968 and 4,136,182. The compound has, in fact, been investigated clinically and studies have been carried out to determine urinary metabolites of this compound. Mass spectrometry techniques were used to investigate the structure of these metabolites and some of this work was described at the Bucknell lecture series (Dec. 1, 1982); at the Thirty-first Annual Conference on Mass Spectrometry and Allied Topics (Boston, 1983); at the Thirty-third Annual Conference on Mass Spectrometry and Allied Topics (San Diego, 1985); and at the Finnigan MAT Seminar Series (Cincinnati, 1985). In these presentations a number of possible metabolites were discussed. 2,3-Dihydro-1-(8-methyl-1,2,4-triazolo[4,3-b]-pyridazin-6-yl)-4(1H)-pyridinone was one of these proposed possible metabolites but the substance involved was only present in small quantities. In addition, it should be noted that the analysis was carried out on urine samples containing a mixture of metabolites rather than on the pure metabolites themselves. Thus, although 2,3-dihydro-1-(8-methyl-1,2,4-triazolo[4,3-b]pyridazin-6-yl)-4(1H)-pyridinone was proposed as a metabolite, it was not isolated in purified form. In addition, at that time, it was not possible to confirm that the structure of this proposed metabolite was correct by independent chemical synthesis. Specifically, because of the dihydropyridinone structure, such a compound could not be obtained by the synthetic procedures described in the patents referred to earlier or by any other obvious alternative procedures.

SUMMARY OF THE INVENTION

The present invention is thus directed to 2,3-dihydro-1-(8-methyl-1,2,4-triazolo [4,3-b]pyridazin-6-yl)-4(1H)-pyridinone itself and in substantially pure form and to methods for the preparation of this compound. It is also directed to the use of this compound as a bronchodilator agent. The present invention is further directed to bronchodilating compositions containing the compound.

It has now been found that the pyridinone referred to above can be prepared by the following series of reactions.

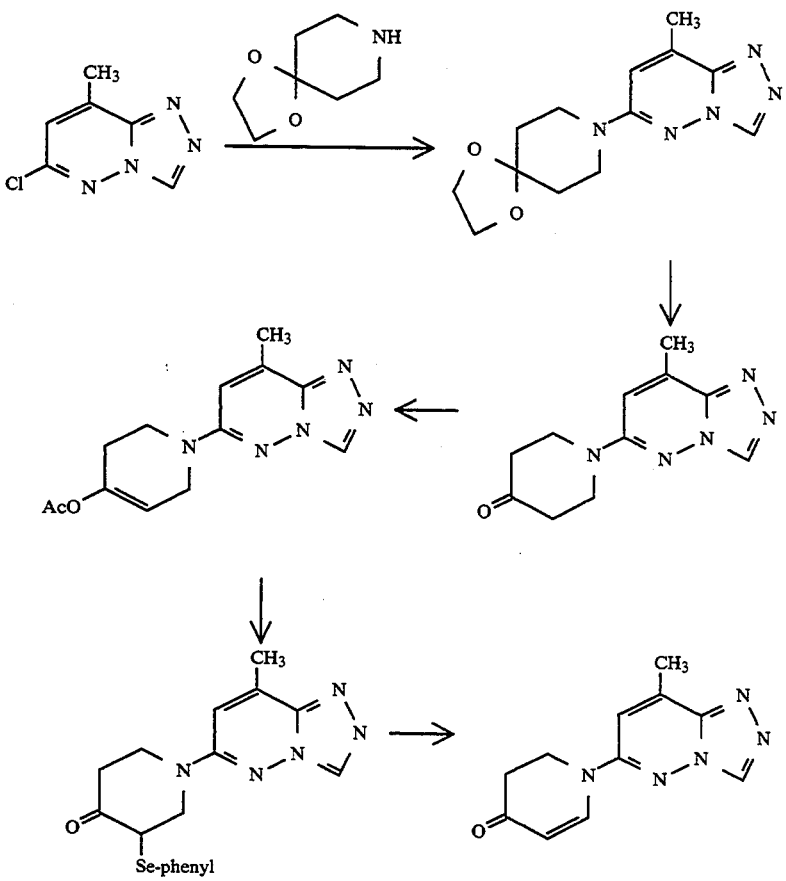

Thus, 6-chloro-8-methyl-1,2,4-triazolo[4,3-b]byridazine is reacted with the ethylene ketal of 4-piperidinone to give the corresponding 6-substituted triazolopyridazine. The ketal function is then hydrolyzed to give the corresponding ketone which is converted to the enol ester. That enol ester is then reacted with phenylselenyl trifluoroacetate (prepared in situ) to give the corresponding α-phenylselenyl ketone. The product is then oxidized with m-chloroperbenzoic acid and treated with base to give the desired product.

An alternative procedure makes use of a tetrahydro pyridine starting material and can be summarized by the following scheme:

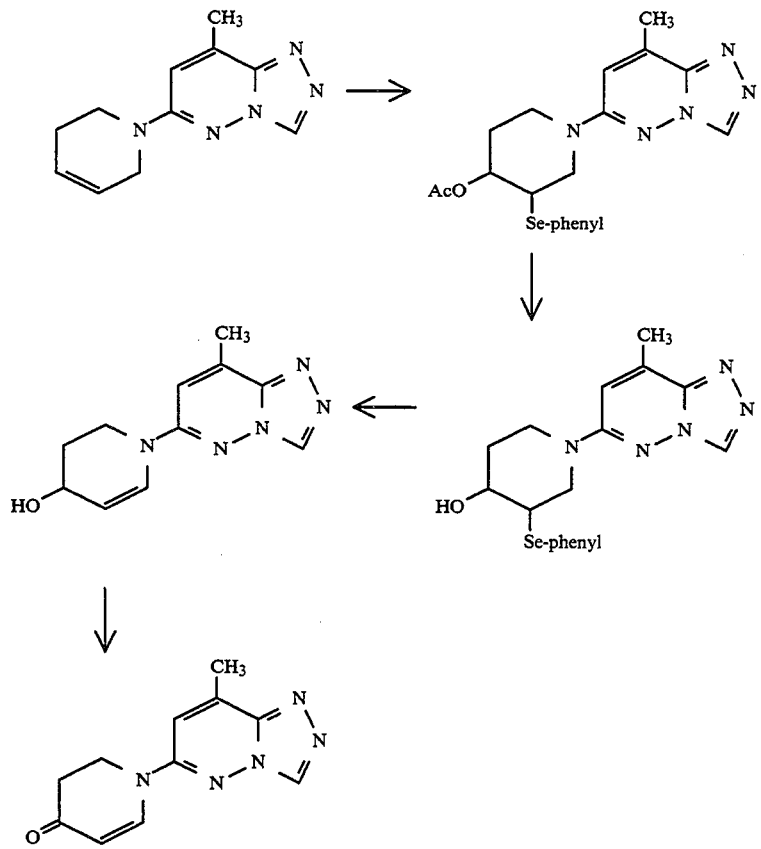

The N-substituted tetrahydropyridine starting material is reacted with phenylselenyl acetate to give the corresponding 4-acetoxy-3-phenylselenylpiperidine which is then hydrolyzed with base to give the corresponding 4-piperidinol. The phenylselenyl compound is then reacted with N-chlorosuccinimide followed by 1,8-diazabicyclo[5,4,0]undec-7-ene to remove the phenylselenyl group and introduce a 2,3-double bond into the piperidine ring. The resulting unsaturated piperidinol is then oxidized with manganese dioxide to give the desired product.

The 2,3-dihydro-1-(8-methyl-1,2,4-triazolo[4,3-b]pyridazin-6-yl)-4(1H) -pyridinone compound as described above is a bronchodilator and is thus useful for the treatment of bronchial disorders such as bronchial asthma. The present invention thus includes a method of effecting bronchodilation using the compound.

In practicing the method of this invention, an effective bronchodilating amount of the 2,3-dihydro-1-(8-methyl-1,2,4-triazolo [4,3-b]pyridazin-6-yl)-4(1H)-pyridinone of this invention is administered internally to a mammal in need thereof by a route effective to bring the compound into contact with the bronchial and tracheal tissues of the mammal. Administration can be carried out either by a parenteral route, such as by intravenous, intraperitoneal, subcutaneous or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the brochodilator activity produced at different dosage rates. More specifically, the compounds can be administered at dosage rates ranging from about 0.1 to about 100 milligrams of the 2,3-dihydro-1-(8-methyl-1,2,4-triazolo[4,3-b]pyridazin--6-yl)-4(1H)--pyridinone compound per kilogram of animal body weight with preferred ranges being from about 0.25 to about 50 or from 1 to 10 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be formulated in conventional time release capsule or tablet formulations although injectable compositions or sprays and aerosols for inhalation are preferred when rapid action is desired. In an example of an individual dosage unit, a tablet would contain 100 mg of active ingredient and would be administered 1 to 6 times, preferably 2 to 4 times daily.

In practicing the method of this invention, the active ingredient is preferably incorporated in a composition comprising a pharmaceutical carrier and from about 5 to about 90 percent by weight of the 2,3-dihydro-1-(8-methyl-1,2,4-triazolo [4,3-b]pyridazin-6-yl)-4(1H)-pyridinone compound. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of composition desired. Suitable pharmaceutical carriers and formulations techniques are found in standard texts, such as Remington's Pharmaceutical Sciences, Mack Publishing Company, Easton, Pa.

Evidence of the bronchodilator activity of the present compound can be obtained from in vitro testing of isolated segments of male guinea pig trachea. This was suspended in a modified Burn solution, aerated with 95% oxygen and 5% carbon dioxide and placed under a tension of 8 g. Tissues were precontracted with one of several contractile agents [histamine ($1 \times 10^{-5}$M), 5-hydroxytryptamine ($2 \times 10^{-6}$M) or potassium chloride (20 mM)] at a concentration that produced 70–80% of its maximal response, previously determined from concentration-contraction curves. Test compound was then added to the baths in a cumulative manner until maximal relaxation responses were obtained. The relaxant effect of each concentration of test compound was expressed as a percentage of that obtained with $3.2 \times 10^{-7}$ isoproterenol and these percentages were used to calculate the $ED_{50}$ of the test compound. All data points consisted of at least five different tissues. Two compounds known to have bronchodilator activity (aminophylline and 8-methyl-6-(1-piperidinyl)-1,2,4-triazolo [4,3-b]pyridazine) were tested at the same time for comparison purposes. The compound of the present invention was found to reverse the contraction produced by the contractile agents, with a potency similar to the piperidinyl compound.

In addition, to evaluate bronchodilator activity, the compound was tested in monkeys. In this procedure, rhesus monkeys were anesthetized, paralyzed, artificially ventilated and prepared for the recording of lung mechanics. Lung resistance was increased by the intravenous infusion of histamine and 2,3-dihydro-1-(8-methyl-1,2,4-triazolo[4,3-b]pyridazin-6-yl)-4(1H)-pyridinone was administered intravenously as a bolus using half-log increasing doses. The subsequent maximal reversals of lung resistance were used to construct a log dose-response curve. From this curve, it was determined that the dihydropyridinone of the present invention had an $ED_{50}$ of approximately 0.18 mg/kg, with the $ED_{50}$ being the dose that gives a 50% reversal of the artificial increase in lung resistance.

The following examples are presented to illustrate the present invention but they should not be construed as limiting it in any way.

EXAMPLE 1

A mixture of 42.1 g 6-chloro-8-methyl-1,2,4-triazolo[[4,3-b]pyridazine, 53.7 g of 4,4-ethylenedioxypiperidine, 50.5 g of triethylamine and 700 ml of absolute ethanol was refluxed under nitrogen for 24 hours. The solvent was removed under reduced pressure and the semi-solid residue obtained was dissolved in about 800 ml of dichloromethane and washed twice with saturated aqueous sodium bicarbonate. The organic phase was then dried over anhydrous sodium sulfate and the solvent was evaporated to leave an orange oil. This oil was dissolved in about 1200 ml of ethyl acetate and then concentrated until crystallization started to take place. The mixture was then cooled to 5° C., the crystalline solid was collected by filtration, washed with fresh ethyl acetate and dried to give 6-(4,4-ethylenedioxy-1-piperidinyl) -8-methyl-1,2,4-triazolo [4,3-b]pyridazine melting at about 156°–157° C.

EXAMPLE 2

A solution of 62.5 g of 6-(4,4-ethylenedioxy-1-piperidinyl)-8-methyl-1,2,4-triazolo [4,3-b]pyridazine in 350 ml of aqueous 10% acetic acid was refluxed for 7 hours. The solvent was then evaporated under reduced pressure and the residue was taken up in 1100 ml of boiling ethanol. The ethanol solution was concentrated to 600 ml and cooled in an ice bath. The crystalline solid which formed was separated by filtration, washed with fresh ethanol and then with ethyl ether and dried to give 1-(8-methyl-1,2,4-triazolo [4,3-b]pyridazin-6-yl)-4-piperidinone as cream-colored needles melting at about 196.5°–199° C.

EXAMPLE 3

A suspension of 23.1 g of 1-(8-methyl-1,2,4-triazolo-[4,3-b]pyridazin-6-yl)-4-piperidinone in 250 ml of acetic anhydride was stirred at room temperature while 22.8 g of 4-toluenesulfonic acid was added in one portion. A clear pale-yellow solution soon developed and this was warmed to about 35° C. After 10 minutes, a while precipitate started to form and the mixture was then heated at 140° C. in an oil bath for 2 hours. Heating was continued for an additional two hours as a stream of nitrogen was passed over the mixture. This resulted in some reduction in volume but the bulk of the acetic anhydride was removed by bulb-to-bulb vacuum distillation (60° C. at about 0.1 mm Hg). The resulting brown gum was dissolved in methylene chloride and washed once with aqueous saturated sodium bicarbonate, then dried over anhydrous sodium sulfate and the solvent was evaporated to leave a brown oil. The oil was chromatographed on silica gel on a Water's associates Prep. 500 liquid chromatograph; the eluent was 95% dichloromethane/5% ethanol with the ethanol containing concentrated ammonium hydroxide in an amount of 10%. This gave a clean product which was 6-(4-acetoxy-1,2,3,6-tetrahydro-1-pyridinyl)-8-methyl-1,2,4-triazolo [4,3-b]pyridazine as a tan solid.

EXAMPLE 4

A suspension of 18.8 g of silver trifluoroacetate in 200 ml of dichloromethane was stirred under nitrogen and heated briefly to reflux in an attempt to dissolve as much solid as possible. However, most of the solid did not dissolve. The resulting suspension was cooled, and to this suspension was added a solution of 14.9 g of phenylselenyl chloride in 100 ml of dichloromethane.

The mixture was stirred vigorously for 90 minutes at room temperature and to the resulting mixture was added, in one portion, 16.4 g of 6-(4-acetoxy-1,2,3,6-tetrahydro-1-pyridinyl)-8-methyl-1,2,4-triazolo [4,3-b]pyridazine in 100 ml of dichloromethane. The mixture was stirred at room temperature and the color soon faded to give a light-yellow suspension. The mixture was first filtered through coarse filter paper and then through a plug of silica gel before it was chromatographed on silica gel on the Water's Prep. 500 instrument; the eluent was 97.5% dichloromethane/2.5% ethanol with the ethanol containing concentrated ammonium hydroxide in an amount of 10%. This gave 1-(8-methyl-1,2,4-triazolo-[4,3-b]pyridazin-6-yl)-3-(phenylselenyl)-4-piperidinone.

EXAMPLE 5

A solution was prepared from 8.8 g of the piperidinone obtained in the preceding example in 400 ml of dichloromethane and 9.4 g of powdered anhydrous potassium carbonate was added to give a suspension. This was stirred at room temperature and there was added a solution of 5.9 g of 3-chloroperoxybenzoic acid in 200 ml of dichloromethane dropwise over a period of 2.5 hours. At the end of the addition, thin layer chromatography showed that the reaction was complete. After filtration through Celite, the solution was evaporated to dryness and the residue was triturated with ether. This dissolved away the selenyl by-products to leave a solid material. Crystallization of this solid from methanol gave 2,3-dihydro-1-(8-methyl-1,2,4-triazolo [4,3-b]pyridazin-6-yl)-4(1H)-pyridinone as yellow needles melting at about 268°–270° C. This compound has the following structure formula:

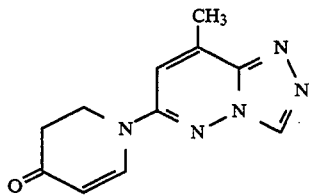

EXAMPLE 6

A solution of 84.3 g of 6-chloro-8-methyl-1,2,4-triazolo [4,3-b]pyridazine, 62.4 g of 1,2,5,6-tetrahydropyridine and 101 g of triethylamine in one liter of ethanol was refluxed under nitrogen for 21 hours. The bulk of the solvent was removed at the rotary evaporator. The residual semi-solid was dissolved in 1000 ml of dichloromethane and washed with 500 ml of saturated sodium bicarbonate solution. The aqueous layer was back washed with fresh dichloromethane (2×200 ml) and the combined organic layers were dried over anhydrous sodium sulfate. Evaporation of the solvent gave a light-brown oil which slowly solidified. This was taken up in 230 ml of hot ethyl acetate and cooled. After cooling the mixture slowly to room temperature and then to 5° C., the cream colored needles which formed were collected, washed with ethyl ether/ethyl acetate (2/1) then with ethyl ether and dried to give 8-methyl-6-(1,2,5,6-tetrahydropyridin-1-yl)-1,2,4-triazolo-[4,3-b]pyridazine melting at about 103°–106° C.

EXAMPLES 7

A mixture of 3.7 g of anhydrous potassium acetate and 3.0 g of diphenyl diselenide in 25 ml of glacial acetic acid was stirred at room temperature while a solution of 1.5 g of bromine in 5 ml of glacial acetic acid was added rapidly. A slight warming of the reaction was noted. The deep red-brown mixture was stirred for 10 minutes and then there was added 4.0 g of 8-methyl-6-(1,2,5,6-tetrahydropyridin-1-yl) -1,2,4-triazolo[4,3-b]pyridazine and stirring at room temperature continued. After 10 minutes, the color of the mixture faded considerably and the reaction was shown to be complete by thin layer chromatography [silica gel, eluted with 95% dichloromethane/5% ethanol (10% concentrated ammonium hydroxide)]. The reaction was diluted with an equal volume of dichloromethane and the inorganic salts filtered off. The filtrate was concentrated to a viscous oil which was subjected to chromatographic purification on a Waters Prep. 500 system with silica gel cartridges and elution with the same solvent system used above for the thin layer chromatography. The clean fractions yielded 4-acetoxy-1-(8-methyl-1,2,4-triazolo [4,3-b]pyridazin-6-yl)-3(phenylselenyl)piperidine as a viscous oil.

EXAMPLE 8

A solution of 3.6 g of 4-acetoxy-1-(8-methyl-1,2,4-triazolo [4,3-b]pyridazin-6-yl)-3-(phenylselenyl)piperidine in 25 ml of ethanol was stirred at room temperature while 10 ml of 1N sodium hydroxide was added. After stirring an additional 30 minutes at room temperature, the reaction was partitioned in water/dichloromethane. The layers were separated, the aqueous phase was washed with fresh dichloromethane and the combined organic layers were dried over anhydrous sodium sulfate and evaporated to give a colorless glass. When this material was boiled in 50 ml of ethyl acetate, a crystalline material formed. After cooling to room temperature, the product was collected and dried to give 1-(8-methyl-1,2,4-triazolo[4,3-b]pyridazin-6-yl)-3-(phenylselenyl)-4-piperidinol melting at about 157°–160° C.

EXAMPLE 9

A solution of 387 mg of 1-(8-methyl-1,2,4-triazolo-[4,3-b]pyridazin-6-yl)-3-(phenylselenyl)-4-piperidinol in dichloromethane at room temperature was treated with a solution of 147 mg of N-chlorosuccinimide in 3 ml of dichloromethane and stirred at room temperature. A white precipitate formed. After 15 minutes, 305 mg of 1,8-diazabicyclo [5,4,0]undec-7-ene was added and stirring continued at room temperature for 20 hours. This resulted in a very dark-colored solution. The reaction volume was reduced at the rotary evaporator and the solution put directly on a silica gel (20 g) flash chromatography column. After rinsing the material on the column with dichloromethane, it was eluted with 95% dichloromethane/5% ethanol (10% concentrated ammonium hydroxide). The clean fractions were combined to give, on evaporation of the solvent, a tan viscous oil which slowly crystallized to give 1-(8-methyl-1,2,4-triazolo[4,3-b]pyridazin-6-yl)-1,4,5,6-tetrahydro-4-pyridinol melting at about 171°–173° C.

EXAMPLE 10

A solution of 116 mg of 1-(8-methyl-1,2,4-triazolo-[4,3-b]pyridazin-6-yl)-1,4,5,6-tetrahydro-4-pyridinol in 15 ml of dichloromethane was treated with 500 ml of manganese dioxide and heated to reflux. The mixture was refluxed for 64 hours and the solids were filtered off through Celite and washed well with fresh hot dichloromethane. Evaporation of the solvent from the filtrate gave 2,3-dihydro-1-(8-methyl-1,2,4-triazolo [4,3-b]pyridazin-6-yl)-4(1H)-pyridinone melting at about 264°-266° C. with decomposition. Crystallization of a portion of this material from methanol gave a purified product as pale yellow needles melting at about 270.5°-271.5° C. with decomposition. This material was identical with the product obtained in Example 5.

What is claimed is:

1. 2,3-Dihydro-1-(8-methyl-1,2,4-triazolo [4,3-b]pyradazin-6-yl)-4(1H)-pyridinone having a melting point of about 270.5°-271.5° C.

2. 2,3-Dihydro-1-(8-methyl-1,2,4-triazolo [4,3-b]pyridazin-6-yl)-4(1H)pyridinone whenever prepared by the process which comprises:
    (a) reacting 6-chloro-8-methyl-1,2,4,triazolo[4,3-b]pyridazine with 4,4-ethylenedioxypiperidine to give 6-(4,4-ethylenedioxy-1-piperidinyl) -8-methyl-1,2,4-triazolo[4,3-b]pyridazine;
    (b) removing the ethylenedioxy protecting group with 10% acetic acid to give the corresponding ketone;
    (c) converting the ketone to the corresponding enol acetate using acetic anhydride and 4-toluenesulfonic acid;
    (d) converting the enol ester to the corresponding α-phenylselenyl ketone using phenylselenyl trifluoroacetate; and,
    (e) reacting the the phenylselenyl compound with 3-chloroperbenzoic acid followed by treatment with base to give the desired product.

3. 2,3-Dihydro-1--(8-methyl-1,2,4-triazolo [4,3-b]pyridazin-6-yl)-4(1H)-pyridinone whenever prepared by the process which comprises:
    (a) reacting 8-methyl-6-(1,2,5,6-tetrahydropyridin-1-yl)-1,2,4triazolo-[4,3-b]pyridazine with phenylselenyl acetate to give 4-acetoxy -1-(8-methyl-1,2,4-triazolo[4,3-b]pyridazin-6-yl)-3-(phenylselenyl)-piperidine;
    (b) hydrolyzing the acetoxy ester group with base to give the corresponding 4-piperidinol;
    (c) reacting the piperidinol first with N-chlorosuccinimide and then with 1,8-diazabicyclo[5.4.0]undec-7-ene to give the corresponding 1,4,5,6-tetrahydro-4-pyridinol; and,
    (d) oxidizing the tetrahydropyridinol with manganese dioxide to give the desired product.

4. A method for alleviating bronchial spasm in mammals which comprises administering to a mammal in need thereof a bronchodilating amount of 2,3-dihydro-1-(8-methyl-1,2,4-triazolo [4,3-b]pyridazin-6-yl)-4(1H)-pyridinone.

5. The method of claim 4 wherein the compound is administered orally at a dosage rate from about 0.25 to about 50 milligrains per kilogram of animal body weight.

6. A composition for use in the treatment of bronchial spasms which comprises 2,3-dihydro-1-(8-methyl-1,2,4-triazolo [4,3-b]pyridazin-6-yl)-4(1H)-pyridinone in a pharmaceutically acceptable carrier.

7. A composition according to claim 6 wherein the pharmaceutically acceptable carrier provides a dosage unit adaptable to oral administration.

* * * * *